(12) United States Patent
Takata et al.

(10) Patent No.: US 11,646,632 B2
(45) Date of Patent: May 9, 2023

(54) CONTROL DEVICE FOR NON-EXCITATION-ACTUATED ELECTROMAGNETIC BRAKE, MULTI-BRAKE SYSTEM, ROBOT, AND MEDICAL ROBOT SYSTEM

(71) Applicants: KAWASAKI JUKOGYO KABUSHIKI KAISHA, Kobe (JP); MEDICAROID CORPORATION, Kobe (JP)

(72) Inventors: Nobuyoshi Takata, Otsu (JP); Hiroaki Harada, Kobe (JP); Tsuyoshi Tagashira, Kakogawa (JP)

(73) Assignees: KAWASAKI JUKOGYO KABUSHIKI KAISHA, Kobe (JP); MEDICAROID CORPORATION, Kobe (JP)

( * ) Notice: Subject to any disclaimer, the term of this patent is extended or adjusted under 35 U.S.C. 154(b) by 718 days.

(21) Appl. No.: 16/726,995

(22) Filed: Dec. 26, 2019

(65) Prior Publication Data

US 2020/0212763 A1 Jul. 2, 2020

(30) Foreign Application Priority Data

Dec. 26, 2018 (JP) .............................. JP2018-243710

(51) Int. Cl.
*H02K 7/102* (2006.01)
*B25J 19/00* (2006.01)
(Continued)

(52) U.S. Cl.
CPC ........... *H02K 7/1025* (2013.01); *A61B 34/30* (2016.02); *B25J 19/0004* (2013.01); *H02P 3/16* (2013.01); *H02P 3/26* (2013.01); *H02P 15/00* (2013.01)

(58) Field of Classification Search
CPC ... H02P 3/16; H02P 3/26; H02P 15/00; A61B 34/30; H02K 7/1025
See application file for complete search history.

(56) References Cited

U.S. PATENT DOCUMENTS

2018/0271732 A1* 9/2018 Yano ...................... A61G 13/04

FOREIGN PATENT DOCUMENTS

| JP | 2014-54695 A | 3/2014 |
|---|---|---|
| JP | 2018-32819 A | 3/2018 |

(Continued)

*Primary Examiner* — Kawing Chan
(74) *Attorney, Agent, or Firm* — Oliff PLC

(57) ABSTRACT

A control device controls non-excitation-actuated electromagnetic brake operation. The control device includes an electronic component having a characteristic that when an inter-terminal voltage of two electrodes is equal to or higher than a predetermined voltage, a resistance value is lower than when the voltage is lower than the voltage and a diode disposed such that a cathode is on a side having a higher potential than an anode. The coil in the non-excitation-actuated electromagnetic brake and the electronic component are connected in series to form a first series circuit, the first series circuit and the diode are connected in parallel, and the electronic component is connected in series with the coil provided in the non-excitation-actuated electromagnetic brake so as not to be conducted when the inter-terminal voltage is lower than the predetermined voltage, but to be conducted when the inter-terminal voltage becomes equal to or higher than the predetermined voltage.

18 Claims, 11 Drawing Sheets

(51) Int. Cl.
    *A61B 34/30*     (2016.01)
    *H02P 3/16*     (2006.01)
    *H02P 3/26*     (2006.01)
    *H02P 15/00*     (2006.01)

(56) References Cited

FOREIGN PATENT DOCUMENTS

| | | | |
|---|---|---|---|
| JP | 2018-113738 A | | 7/2018 |
| JP | 2018113738 A | * | 7/2018 |
| JP | 2018-158009 A | | 10/2018 |

* cited by examiner

[FIG. 1]

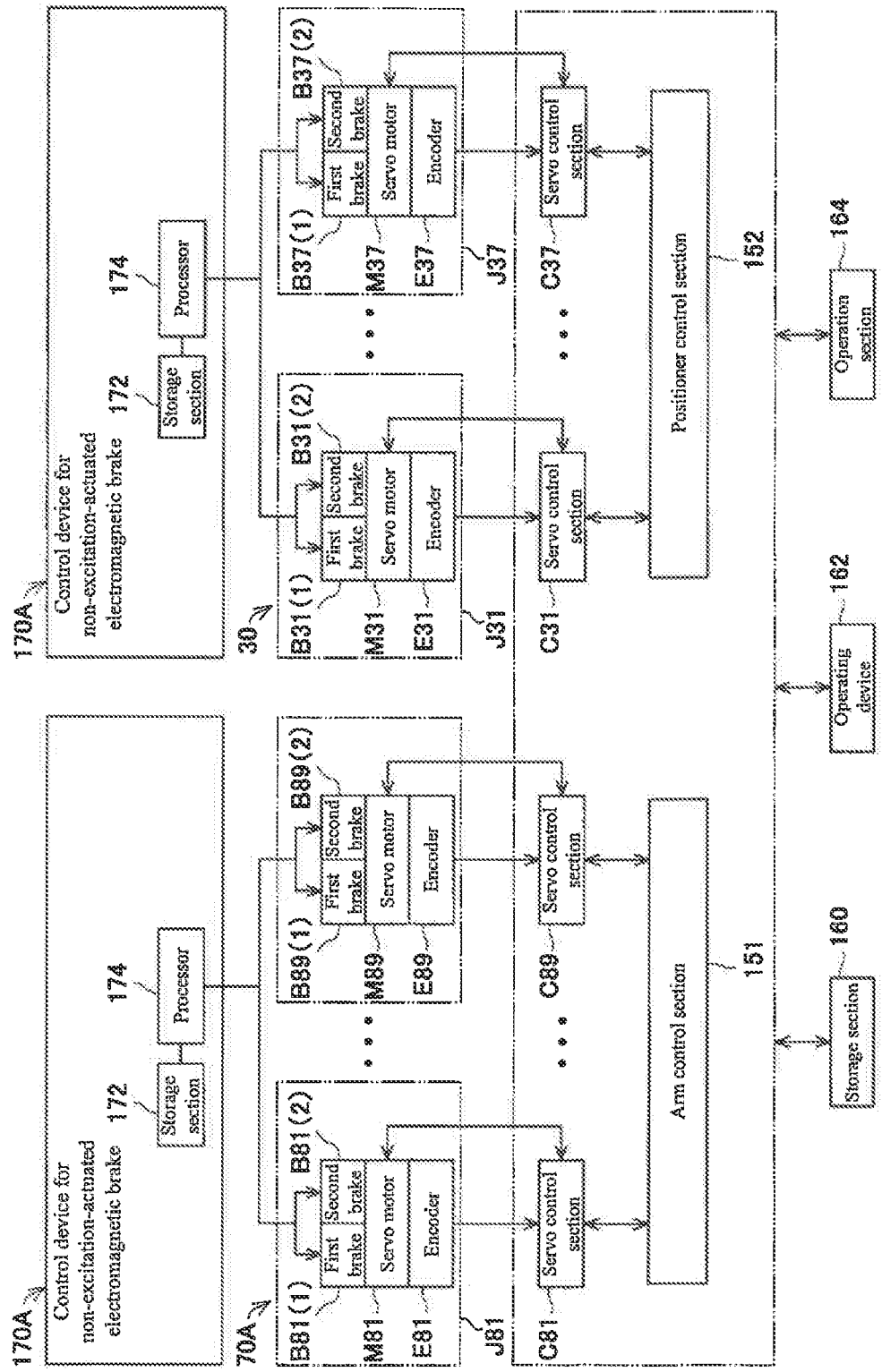
[FIG. 3]

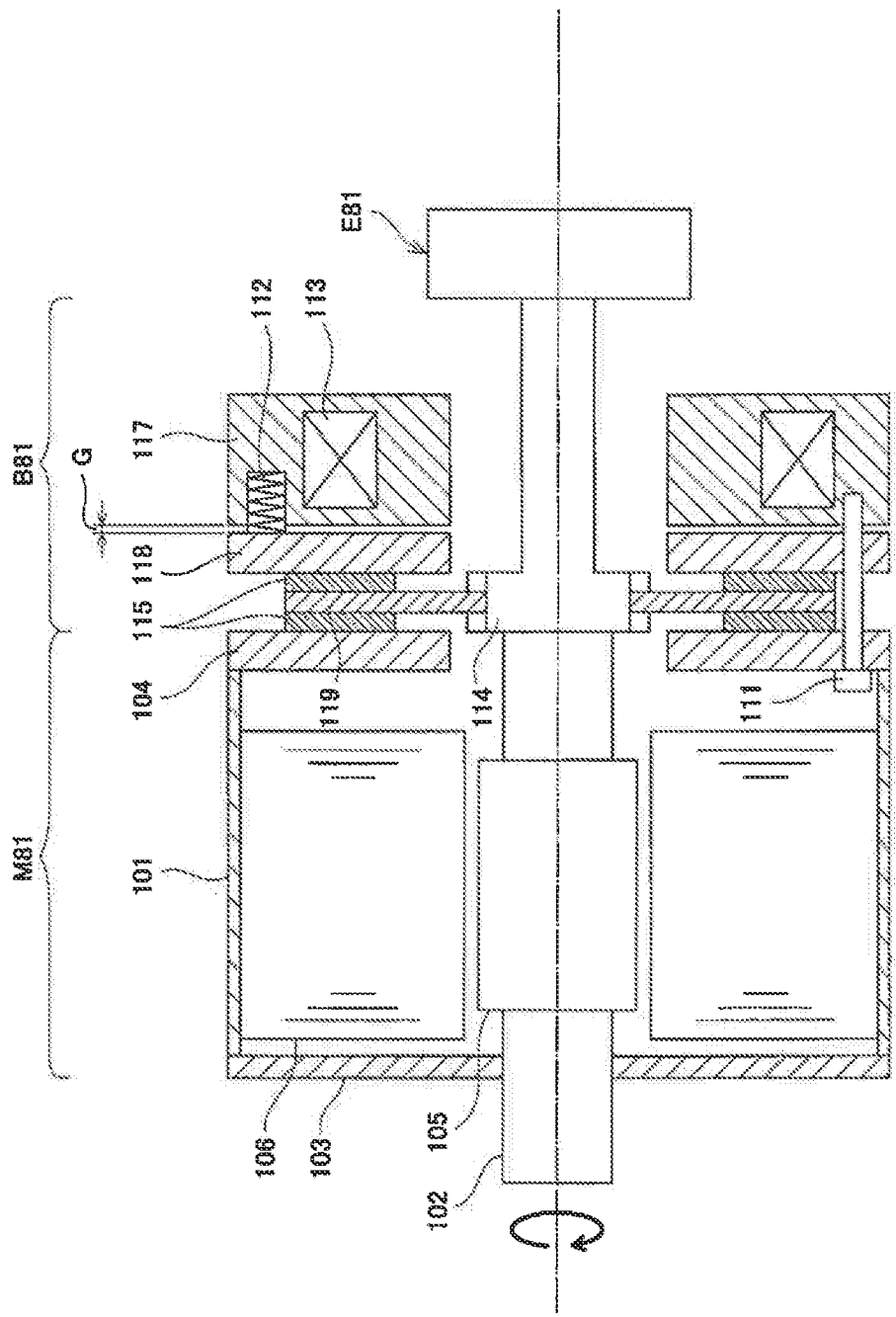

[FIG. 5]
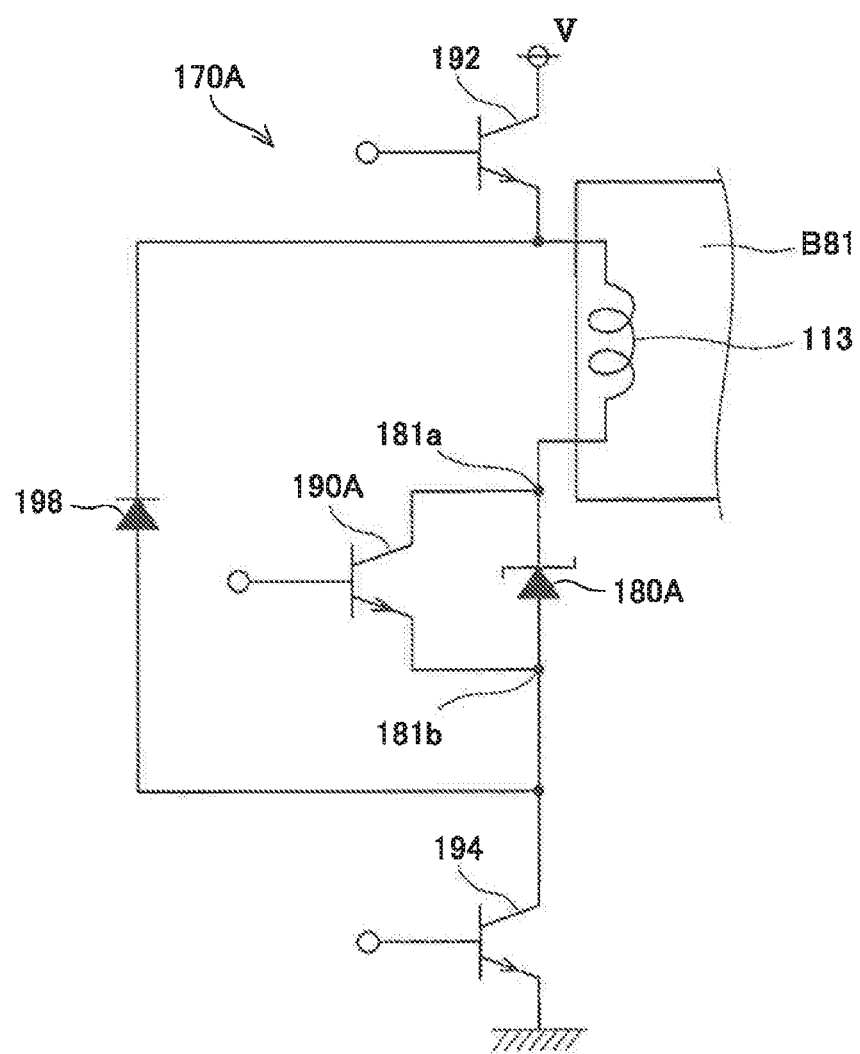

[FIG. 6]
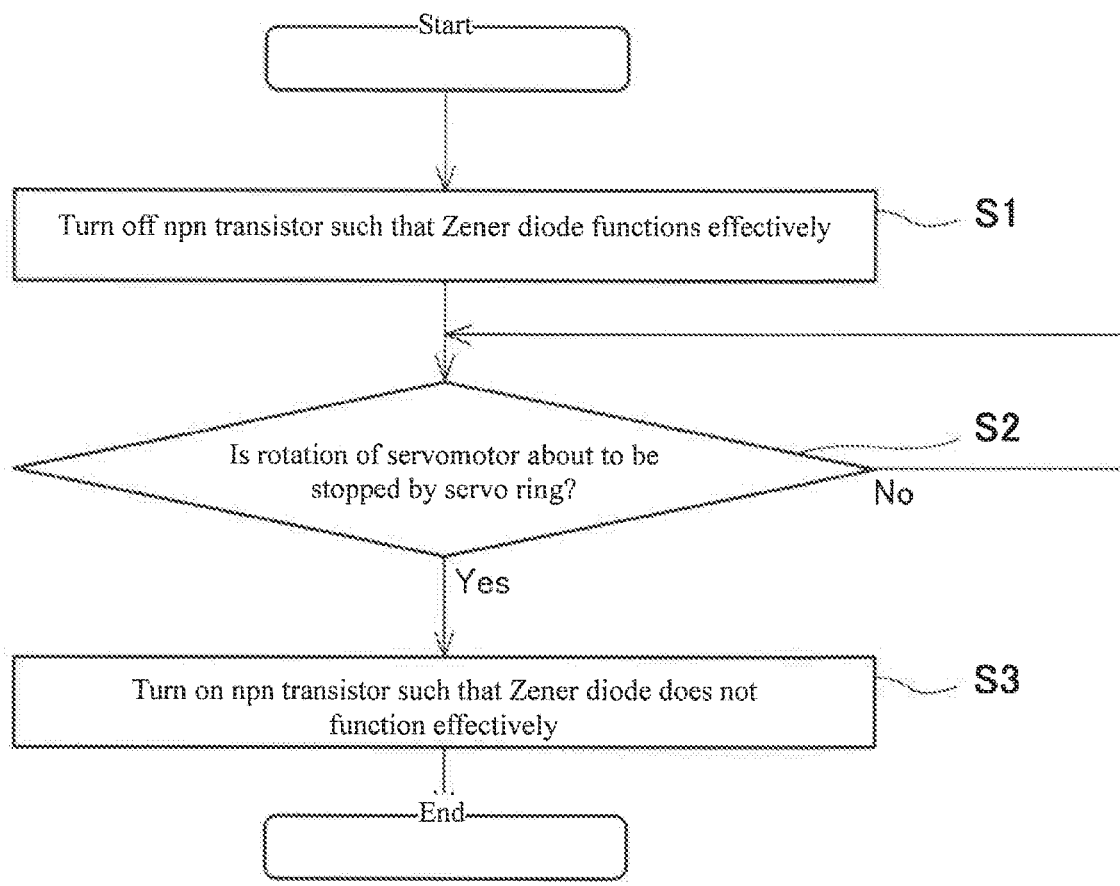

[FIG. 7]
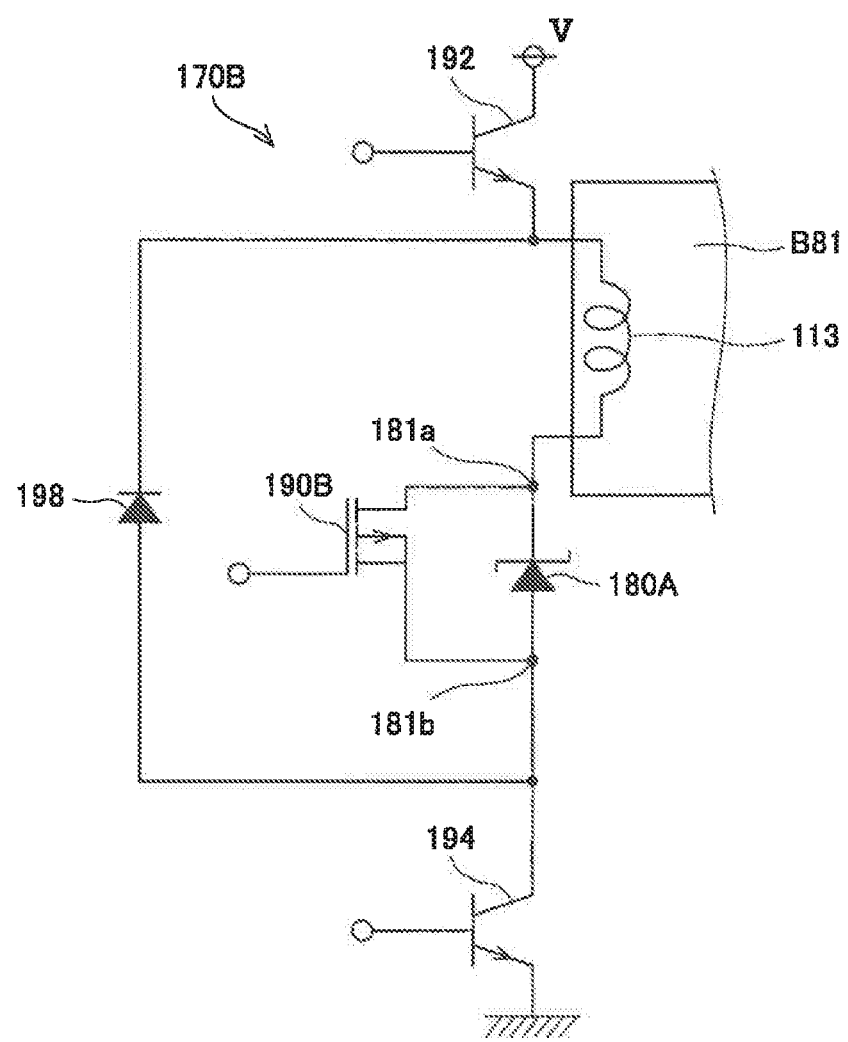

[FIG. 8]
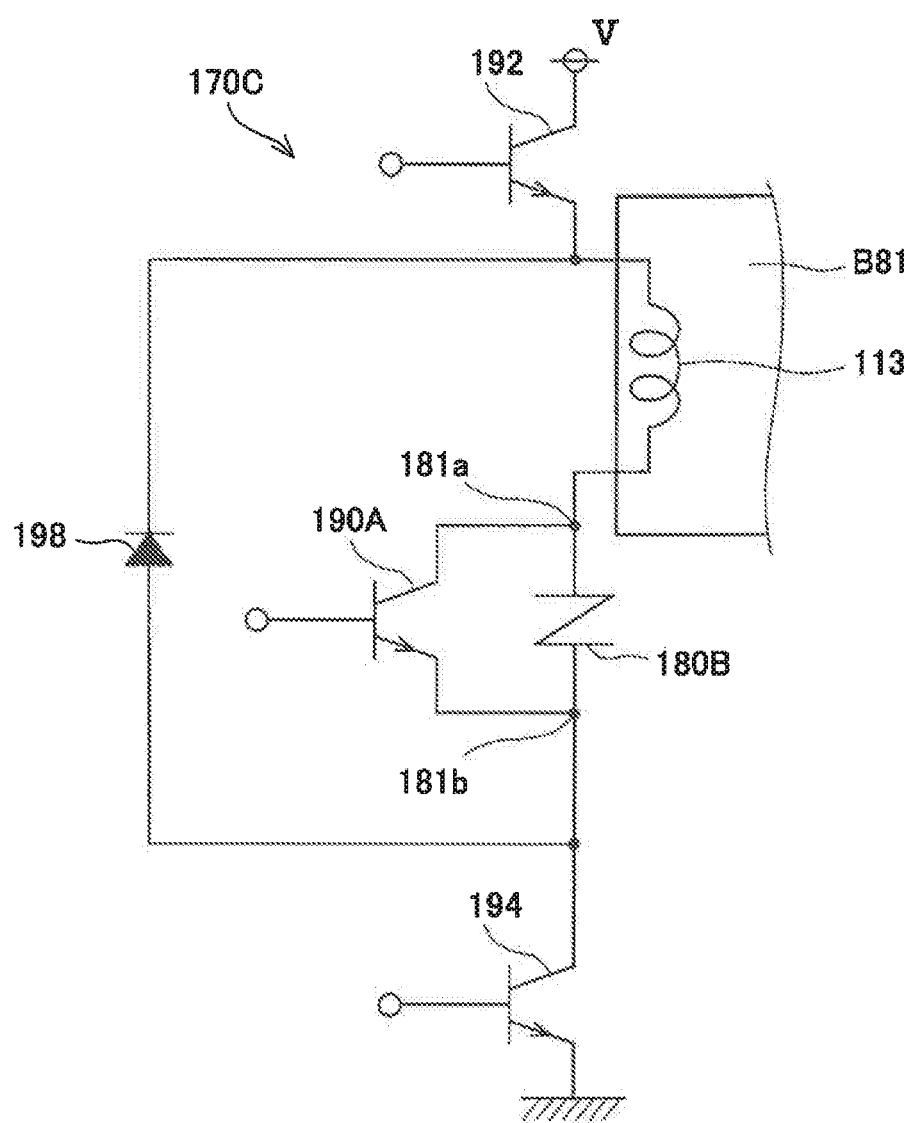

[FIG. 9]
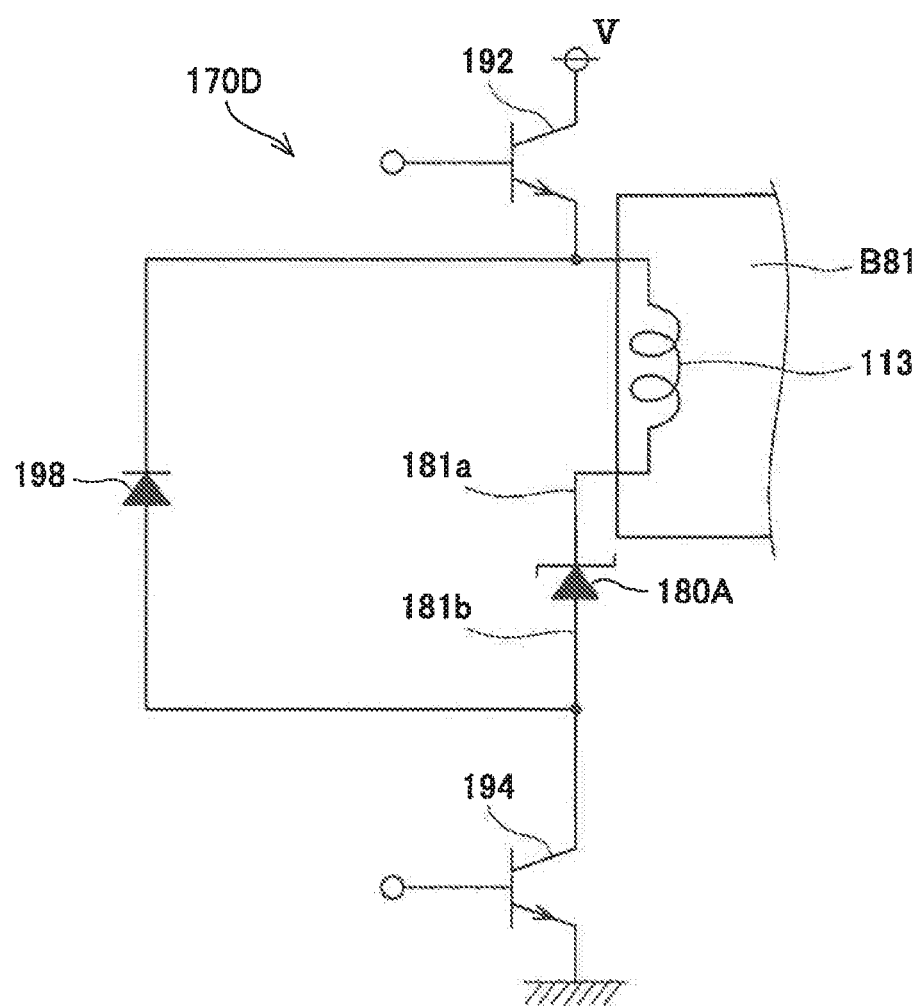

[FIG. 10A]
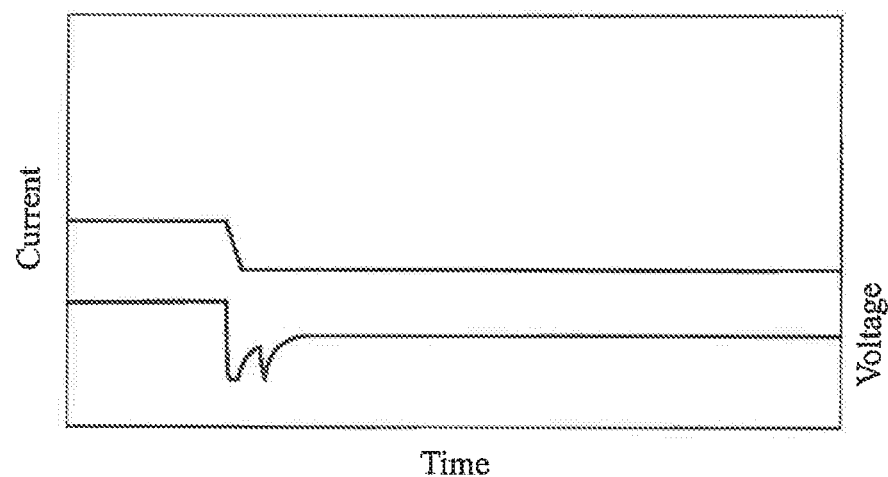
[FIG. 10B]
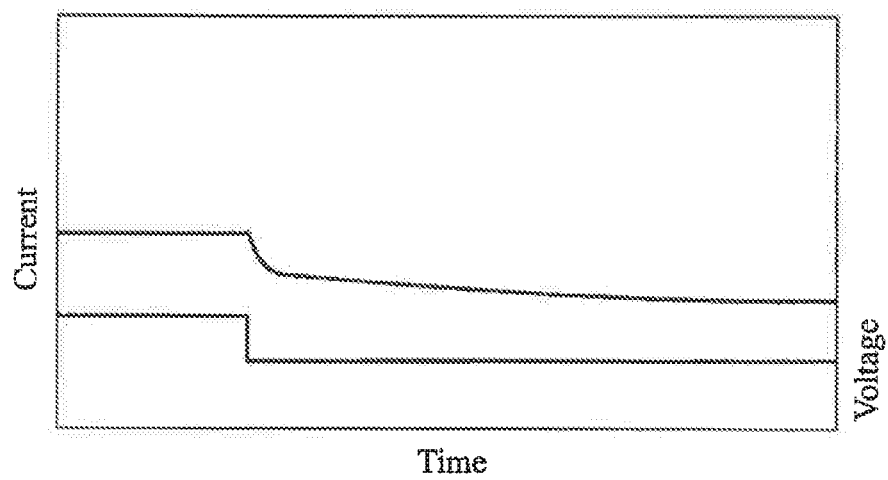

[FIG. 11]
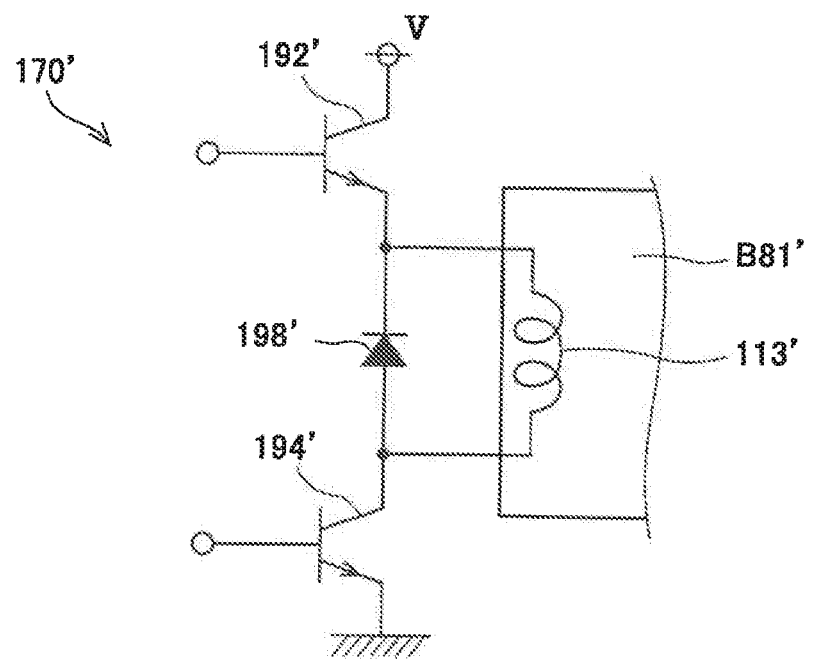

CONTROL DEVICE FOR NON-EXCITATION-ACTUATED ELECTROMAGNETIC BRAKE, MULTI-BRAKE SYSTEM, ROBOT, AND MEDICAL ROBOT SYSTEM

TECHNICAL FIELD

The present invention relates to a control device for a non-excitation-actuated electromagnetic brake, a multi-brake system, a robot, and a medical robotic system.

BACKGROUND ART

Conventionally, there is known a control device for controlling operation of a non-excitation-actuated electromagnetic brake configured to apply a brake when a coil is in a non-excited state and not to apply the brake when the coil is in an excited state. Such a control device for a non-excitation-actuated electromagnetic brake has been proposed in, for example, a brake release circuit of an industrial robot disclosed in Japanese Patent Application Laid-Open No. 2014-54695.

The above publication describes a non-excitation-actuated electromagnetic brake provided on a joint shaft of a robot arm. The control device for a non-excitation-actuated electromagnetic brake described in the above publication switches a power supply from an internal power supply to an emergency power supply using a connector, and supplies power from the emergency power supply to excite a coil, and thus to release a brake.

SUMMARY OF INVENTION

By the way, conventionally, in order to prevent a surge current from flowing through a coil provided in a non-excitation-actuated electromagnetic brake, a circuit configuration in which a diode is connected in parallel to the coil has been known. FIG. 11 is a circuit diagram showing a configuration of a main portion of a conventional control device for a non-excitation-actuated electromagnetic brake. A control device 170' has a circuit configuration as shown in FIG. 11, and thus can prevent a surge current from flowing through a coil 113' provided in a non-excitation-actuated electromagnetic brake B81'.

However, in the circuit configuration as shown in FIG. 11, for example, at least one of npn transistors 192' and 194' is turned off from a state where both of the npn transistors 192' and 194' are turned on, and when an attempt is made to switch the coil 113' to a non-excited state, a back electromotive force is generated in the coil 113', so that a return current flows through a diode 198'. Due to this, in the control device for a non-excitation-actuated electromagnetic brake described in the above publication and the conventional one, a delay may occur until the brake is applied.

Thus, an object of the present invention is to provide a control device for a non-excitation-actuated electromagnetic brake, multi-brake system, a robot, and a medical robotic system, capable of preventing a surge current from flowing through a coil provided in the non-excitation-actuated electromagnetic brake and preventing a delay from occurring until the brake is applied.

In order to solve the above-mentioned problems, a control device for a non-excitation-actuated electromagnetic brake according to the present invention is a control device for controlling operation of a non-excitation-actuated electromagnetic brake, which is configured to apply the brake when a coil is in a non-excited state and not to apply the brake when the coil is in an excited state. The control device includes an electronic component including two electrodes and having a characteristic that when an inter-terminal voltage of the two electrodes is equal to or higher than a predetermined voltage, a resistance value is lower than when the voltage is lower than the predetermined voltage and a diode disposed such that a cathode is located on a side having a higher potential than an anode. The coil provided in the non-excitation-actuated electromagnetic brake and the electronic component are connected in series to form a first series circuit, the first series circuit and the diode are connected in parallel, and the electronic component is connected in series with the coil provided in the non-excitation-actuated electromagnetic brake so as not to be conducted when the inter-terminal voltage is lower than the predetermined voltage, but to be conducted when the inter-terminal voltage becomes equal to or higher than the predetermined voltage.

According to the above configuration, the control device according to the present invention can prevent a surge current from flowing through the coil by connecting the diode in parallel with the coil provided in the non-excitation-actuated electromagnetic brake. The control device according to the present invention includes an electronic component connected in series with the coil so as not to be conducted when the inter-terminal voltage is lower than the predetermined voltage, but to be conducted when the inter-terminal voltage becomes equal to or higher than the predetermined voltage, so that it is possible to prevent a return current from flowing through the coil. Consequently, it is possible to prevent a delay from occurring until the brake is applied.

For example, the electronic component may be a Zener diode or a varistor.

The predetermined voltage may be set to 120% or more and 200% or less of an excitation voltage applied to the coil, provided in the non-excitation-actuated electromagnetic brake, in order to bring the coil into an excited state.

According to the above configuration, it is possible to further suppress the occurrence of a delay until the brake is applied, as compared with a case where the predetermined voltage is less than 120% of the excitation voltage. Further, noise can be suppressed as compared with a case where the predetermined voltage is higher than 200% of the excitation voltage.

The control device according to the present invention may further include a switching element connected in parallel with the electronic component so as to be a bypass for the electronic component and capable of switching a state between a state where the electronic component functions effectively and a state where the electronic component does not function.

According to the above configuration, it is possible to switch a state between the state where the electronic component functions effectively and the state where the electronic component does not function according to the situation.

The switching element may be a transistor or a field effect transistor.

For example, the non-excitation-actuated electromagnetic brake may be attached to the motor to apply the brake to the motor.

In the control device according to the present invention, the motor is a servomotor, and the control device further includes a storage section and a processor for executing a program stored in the storage section. When the program stored in the storage section is executed by the processor, and when rotation of the servomotor is about to be stopped by a servo ring, the switching element may be turned on so that the electronic component does not function effectively.

According to the above configuration, it is possible to prevent wear from occurring between the servomotor and the non-excitation-actuated electromagnetic brake, and to suppress noise that may occur when the non-excitation-actuated electromagnetic brake is applied quickly.

In order to solve the above-mentioned problem, the multi-brake system according to the present invention is a multi-brake system including a plurality of non-excitation-actuated electromagnetic brakes, a control device for controlling operation of each of the plurality of non-excitation-actuated electromagnetic brakes is provided, and the control device is the control device for a non-excitation-actuated electromagnetic brake according to any one of claims 1 to 6.

According to the above configuration, the multi-brake system according to the present invention includes any of the above-described control devices for a non-excitation-actuated electromagnetic brake, so that it is possible to prevent a surge current from flowing through a coil provided in the non-excitation-actuated electromagnetic brake and prevent a delay from occurring until the brake is applied. Since any of the above-described control devices for a non-excitation-actuated electromagnetic brake is provided to control the operation of each of the plurality of non-excitation-actuated electromagnetic brakes, safety can be improved.

In order to solve the above problems, a robot according to the present invention includes any of the above-described control devices for a non-excitation-actuated electromagnetic brake, the non-excitation-actuated electromagnetic brake, the motor to which the non-excitation-actuated electromagnetic brake is attached, a robot arm having at least one joint shaft driven by the motor, and a robot control device for controlling operation of the motor.

According to the above configuration, the robot according to the present invention includes any of the above-described control devices for a non-excitation-actuated electromagnetic brake, so that it is possible to prevent a surge current from flowing through a coil provided in the non-excitation-actuated electromagnetic brake and prevent a delay from occurring until the brake is applied.

The multi-brake system described above may be provided.

According to the above configuration, since any of the above-described control devices for a non-excitation-actuated electromagnetic brake is provided to control the operation of each of the plurality of non-excitation-actuated electromagnetic brakes, safety can be improved.

The control device for a non-excitation-actuated electromagnetic brake may be configured as a part of the robot control device.

According to the above configuration, the robot according to the present invention can have a simple configuration.

In order to solve the above problems, a medical robotic system according to the present invention includes any one of the robots described above.

According to the above configuration, the medical robotic system according to the present invention includes any of the robots described above, so that it is possible to prevent a surge current from flowing through a coil provided in the non-excitation-actuated electromagnetic brake and prevent a delay from occurring until the brake is applied.

In order to solve the above-mentioned problems, a medical robotic system according to the present invention includes a robot arm including a non-excitation-actuated electromagnetic brake, which applies a brake when a coil is in a non-excited state and does not apply the brake when the coil is in an excited state, a motor to which the non-excitation-actuated electromagnetic brake is attached, and a joint shaft driven by the motor, a robot control device which controls operation of the motor, and a control device for a non-excitation-actuated electromagnetic brake for controlling operation of the non-excitation-actuated electromagnetic brake. The control device for a non-excitation-actuated electromagnetic brake includes an electronic component including two electrodes and having a characteristic that when an inter-terminal voltage of the two electrodes is equal to or higher than a predetermined voltage, a resistance value is lower than when the voltage is lower than the predetermined voltage and a diode disposed such that a cathode is located on a side having a higher potential than an anode. The coil and the electronic component are connected in series to form a first series circuit, the first series circuit and the diode are connected in parallel, and the electronic component is connected in series with the coil provided in the non-excitation-actuated electromagnetic brake such that the electronic component is not conducted when the inter-terminal voltage is lower than the predetermined voltage, but conducted when the inter-terminal voltage becomes equal to or higher than the predetermined voltage.

According to the above configuration, the medical robotic system according to the present invention includes the above-described control devices for a non-excitation-actuated electromagnetic brake, so that it is possible to prevent a surge current from flowing through a coil provided in the non-excitation-actuated electromagnetic brake and prevent a delay from occurring until the brake is applied.

The medical robotic system according to the present invention includes an instruction device that allows an operator to remotely operate the robot arm. The robot arm holds a medical instrument at a distal end, and the robot control device may control operation of the motor to operate the robot arm based on operation of the instruction device.

For example, the electronic component may be a Zener diode or a varistor.

The predetermined voltage may be set to 120% or more and 200% or less of an excitation voltage applied to the coil, provided in the non-excitation-actuated electromagnetic brake, in order to bring the coil into an excited state.

According to the above configuration, it is possible to further suppress the occurrence of a delay until the brake is applied, as compared with a case where the predetermined voltage is less than 120% of the excitation voltage. Further, noise can be suppressed as compared with a case where the predetermined voltage is higher than 200% of the excitation voltage.

The control device according to the present invention may further include a switching element connected in parallel with the electronic component so as to be a bypass for the electronic component and capable of switching a state between a state where the electronic component functions effectively and a state where the electronic component does not function.

According to the above configuration, it is possible to switch a state between the state where the electronic component functions effectively and the state where the electronic component does not function according to the situation.

For example, the switching element may be a transistor or a field effect transistor.

In the control device according to the present invention, the motor is a servomotor, and the control device further includes a storage section and a processor for executing a program stored in the storage section. When the program stored in the storage section is executed by the processor, and when rotation of the servomotor is about to be stopped by a servo ring, the switching element may be turned on so that the electronic component does not function effectively.

According to the above configuration, it is possible to prevent wear from occurring between the servomotor and the non-excitation-actuated electromagnetic brake, and to suppress noise that may occur when the non-excitation-actuated electromagnetic brake is applied quickly.

The robot arm may include a plurality of the joint shafts, a plurality of the motors, and a plurality of the non-excitation-actuated electromagnetic brakes, and may include a plurality of the control devices for a non-excitation-actuated electromagnetic brake.

According to the above configuration, since any of the above-described control devices for a non-excitation-actuated electromagnetic brake is provided to control the operation of each of the plurality of non-excitation-actuated electromagnetic brakes, safety can be improved.

The above and further objects, features and advantages of the present invention will more fully be apparent from the following detailed description of preferred embodiments with accompanying drawings.

BRIEF DESCRIPTION OF DRAWINGS

FIG. 3 is a block diagram showing a configuration of a control system provided in the medical manipulator according to one embodiment of the present invention.

FIG. 4 is a cross-sectional view along an axial direction showing an internal configuration of each of a servomotor, an encoder, and a non-excitation-actuated electromagnetic brake provided in the medical manipulator according to one embodiment of the present invention.

FIG. 5 is a circuit diagram showing a configuration of a main portion of a control device for a non-excitation-actuated electromagnetic brake according to one embodiment of the present invention.

FIG. 6 is a flowchart showing an example of processing executed by the control device for a non-excitation-actuated electromagnetic brake according to one embodiment of the present invention.

FIG. 7 is a circuit diagram showing a configuration of a main portion of a first modification of the control device for a non-excitation-actuated electromagnetic brake according to one embodiment of the present invention.

FIG. 8 is a circuit diagram showing a configuration of a main portion of a second modification of the control device for a non-excitation-actuated electromagnetic brake according to one embodiment of the present invention.

FIG. 9 is a circuit diagram showing a configuration of a main portion of a third modification of the control device for a non-excitation-actuated electromagnetic brake according to one embodiment of the present invention.

FIG. 10A is a graph showing results of an experiment performed by the present inventors to confirm an effect of the control device for a non-excitation-actuated electromagnetic brake according to one embodiment of the present invention, and a graph when a coil is switched to a non-excited state after a Zener diode is enabled.

FIG. 10B is a graph showing results of the experiment performed by the present inventors to confirm the effect of the control device for a non-excitation-actuated electromagnetic brake according to one embodiment of the present invention, and a graph when the coil is switched to the non-excited state after the Zener diode is disabled.

FIG. 11 is a circuit diagram showing a configuration of a main portion of a conventional control device for a non-excitation-actuated electromagnetic brake.

DESCRIPTION OF EMBODIMENTS (Surgical Operation System 10)

Hereinafter, a control device for a non-excitation-actuated electromagnetic brake, a multi-brake system, a robot, and a medical robotic system according to an embodiment of the present invention will be described with reference to the accompanying drawings. The present invention is not limited by the embodiment. In the following explanations and drawings, the same reference signs are used for the same or corresponding components, and a repetition of the same explanation is avoided.

Figure 1:
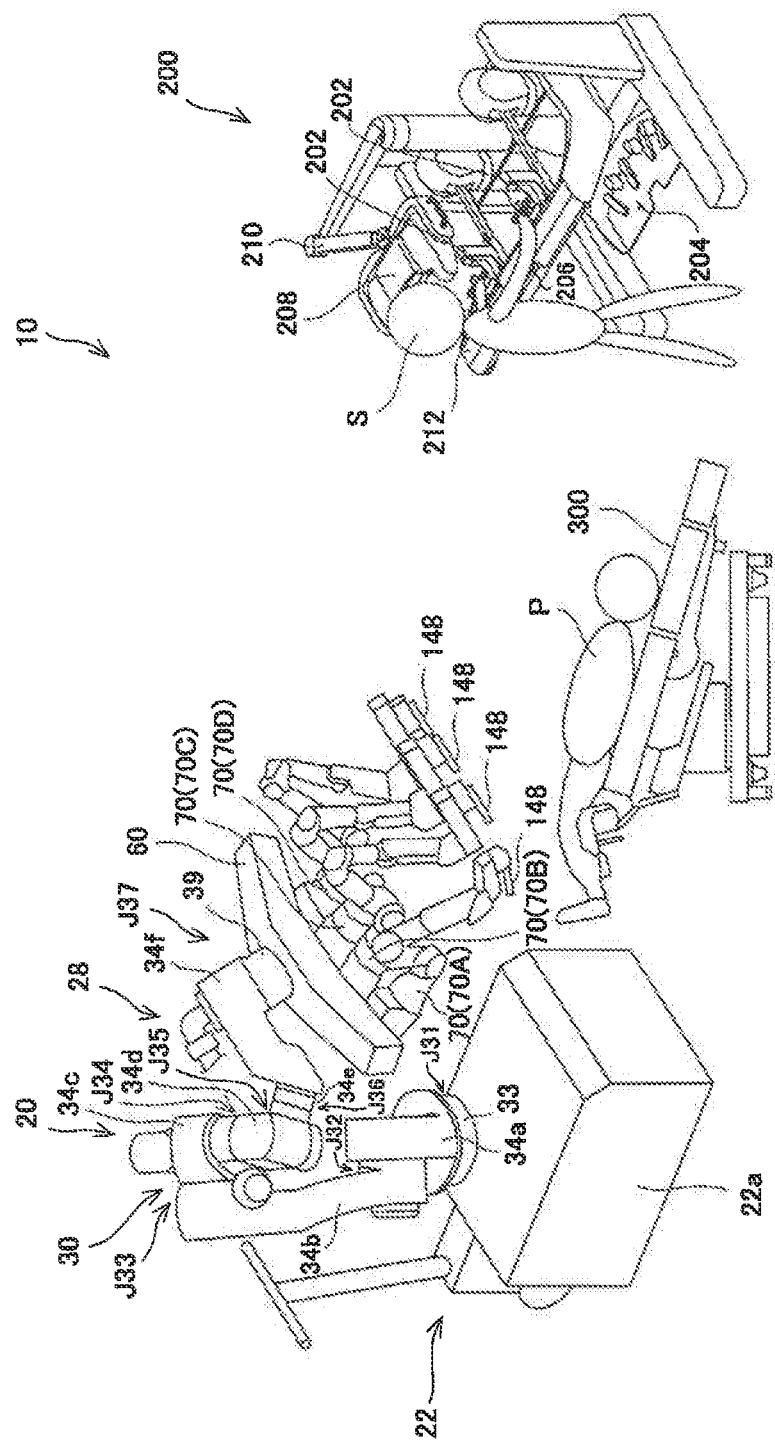
FIG. 1 is a schematic view showing a usage of a medical manipulator according to one embodiment of the present invention.

FIG. 1 is a schematic view showing a usage of a medical manipulator according to the present embodiment. As shown in FIG. 1, a medical manipulator 20 (robot) according to the present embodiment is provided in a surgical operation system 10 (medical robotic system). The surgical operation system 10 is a system used when a practitioner S such as a doctor performs an endoscopic surgical operation to a patient P on an operating table 300, such as robot assisted operation or robot remote operation.

The surgical operation system 10 includes the medical manipulator 20 (robot), which is a patient-side system, and an instruction device 200 for operating a plurality of robot arms 70, which will be described later, of the medical manipulator 20. The instruction device 200 is disposed apart from the medical manipulator 20, and the medical manipulator 20 is remotely operated by the instruction device 200.

The practitioner S inputs an operation to be performed by the medical manipulator 20 to the instruction device 200, and the instruction device 200 transmits this operation command to the medical manipulator 20. The medical manipulator 20 receives the operation command transmitted from the instruction device 200, and operates a plurality of robot arms 70, which will be described later, based on the operation command.

A medical trolley 22 stores inside a robot control device 150 and a storage section 160 for storing programs and various data used for operation control. The medical trolley 22 is provided with an operation section 164 for setting and inputting positions and postures of a positioner 30, an arm base 60 and the plurality of robot arms 70 mainly before an operation.

The instruction device 200 may be disposed inside or outside an operating room. The instruction device 200 includes, for example, an operation arm 202 for the practitioner S to input an operation command, an operation pedal 204, a touch panel 206, a monitor 208 for displaying an image captured by an endoscope assembly, a support arm 210 for supporting the monitor 208 at a height position of the face of an operator such as a doctor, and a bar 212 on which the touch panel 206 is disposed.

The practitioner S operates the operation arm 202 and the operation pedal 204 while visually confirming an affected part on the monitor 208, and inputs an operation command to the instruction device 200. The operation command input to the instruction device 200 is transmitted to the robot control device 150 of the medical manipulator 20 by wire or wirelessly. Operation of the medical manipulator 20 is controlled by the robot control device 150. The robot control device 150 may have a configuration realized by, for example, the fact that a known processor (CPU or the like) operates according to a program stored in a storage section (memory or the like).

(Medical Manipulator 20)

In FIG. 1, the medical manipulator 20 is placed in an operating room, which is a sterile field. The medical manipulator 20 includes the positioner 30, the elongated arm base 60 attached to a distal end of the positioner 30, and a plurality of (four in this embodiment) multi-degree-of-freedom robot arms 70 whose proximal end is detachably attached to the arm base 60. The medical manipulator 20 is configured such that the plurality of robot arms 70 assume a folded storage position.

The positioner 30 is configured as a vertical articulated-type robot, is provided on a base body 22a of the medical trolley 22 disposed at a predetermined position in the operating room, and can move the position of the arm base 60 three-dimensionally. The arm base 60 and the robot arm 70 are covered with a sterile drape (not shown) to be shielded from the sterile field in the operating room.

The positioner 30 includes a base 33 attached to an upper surface of the medical trolley 22, and a plurality of positioner links sequentially connected from the base 33 toward the distal end. The positioner 30 constitutes a plurality of joint shafts by sequentially connecting the positioner links such that one positioner link rotates with respect to another positioner link. The plurality of positioner links include links 34a to 34f. The plurality of joint shafts include a joint shaft J31 to a joint shaft J37. Although the plurality of joints in the present embodiment are constituted by a rotating joint having a rotating shaft, at least some joints may be constituted by a linear joint.

More specifically, a proximal end of the link 34a is connected to the distal end of the base 33 through the joint shaft J31 that is a torsion (roll) joint. A proximal end of the link 34b is connected to a distal end of the link 34a through the joint shaft J32 that is a bending (pitch) joint. A proximal end of the link 34c is connected to a distal end of the link 34b through the joint shaft J33 that is a bending joint. A proximal end of the link 34d is connected to a distal end of the link 34c through the joint shaft J34 that is a torsion joint. A proximal end of the link 34e is connected to a distal end of the link 34d through the joint shaft J35 that is a bending joint. A proximal end of the link 34f is connected to a distal end of the link 34e through the joint shaft J36 that is a torsion joint. A positioner mounting portion 39 of the arm base 60 is connected to a distal end of the link 34f through the joint shaft J37 that is a torsion joint. Thus, the positioner 30 is configured as a multi-axis articulated (seven-axis articulated) arm with a plurality of degrees of freedom (seven degrees of freedom).

At a distal end of the robot arm 70A among the plurality of robot arms 70, for example, a replacement instrument (for example, forceps) is held as a medical instrument 140. At a distal end of the robot arm 70B, an instrument such as a forceps is held as the medical instrument 140. At a distal end of the robot arm 70C, for example, an endoscope assembly is held as the medical instrument 140. At a distal end of the robot arm 70D, for example, an endoscope assembly for replacement is held as the medical instrument 140.

The arm base 60 has a function as a hub serving as a base for the plurality of robot arms 70. In the present embodiment, the positioner 30 and the arm base 60 constitute an arm support 28 that movably supports the plurality of robot arms 70. In the medical manipulator 20, the respective constituent elements ranging from the positioner 30 to the medical instrument 140 are connected in series. Hereinafter, in this specification, in the above-described series of constituent elements, the positioner 30 side is referred to as a proximal end, and the medical instrument 140 side is referred to as a distal end.

Figure 2:
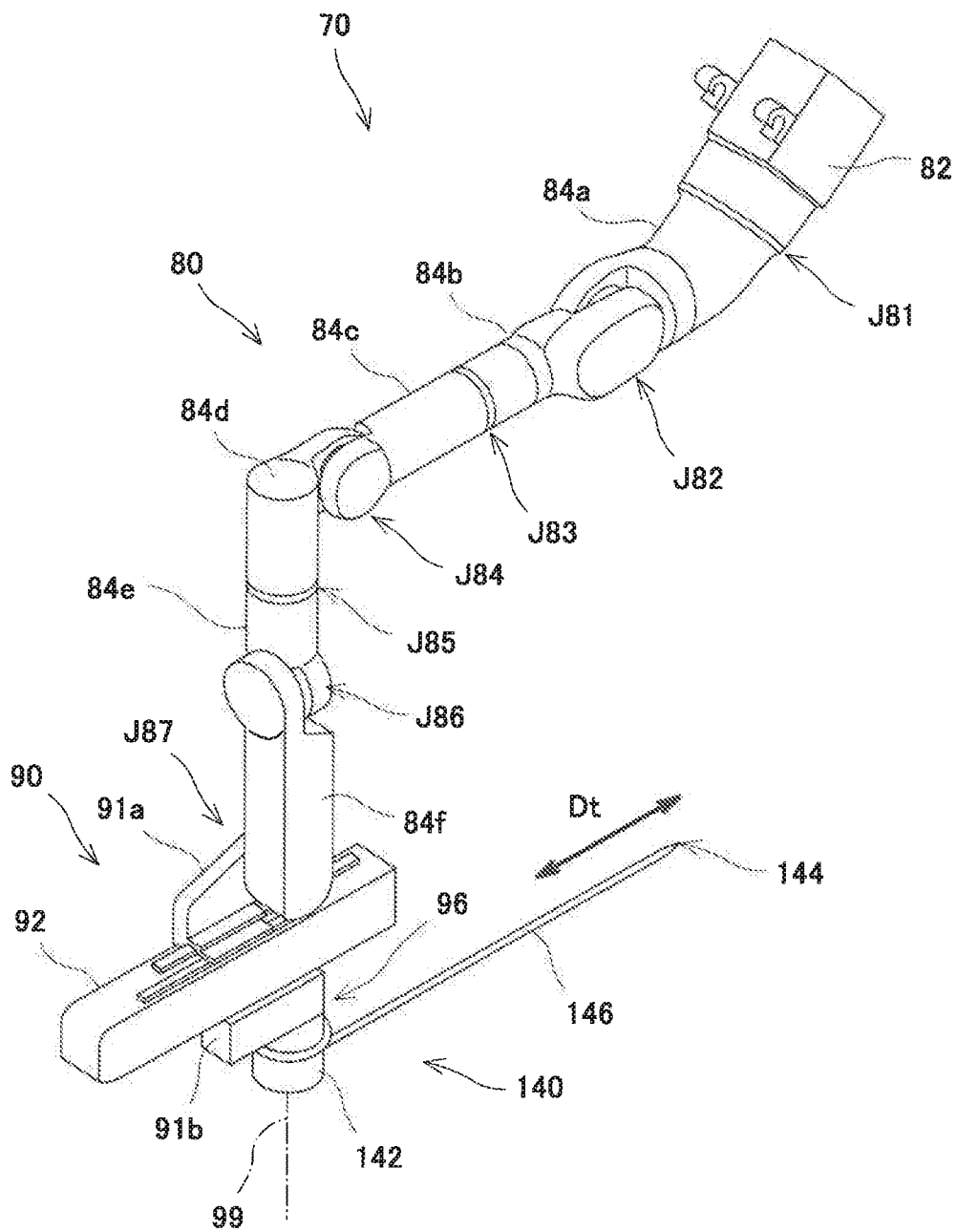
FIG. 2 is a schematic view showing a configuration of a robot arm provided in the medical manipulator according to one embodiment of the present invention.

As shown in FIG. 2, when the medical instrument 140 is an instrument, the medical instrument 140 has a drive unit 142 at a proximal end thereof. An end effector provided at a distal end of the instrument is selected from a group consisting of an instrument having an operable joint (for example, forceps, scissors, a grasper, a needle holder, a microdissector, a staple applier, a tucker, a siphonage tool, a snare wire, a clip applier, etc.), and an instrument without a joint (for example, a cutting blade, a cautery probe, a washer, a catheter, a suction orifice, etc.).

In an operation using the medical manipulator 20, first, the medical trolley 22 is moved to a predetermined position in the operating room by a medical personnel. In this case, the medical trolley 22 moved to the predetermined position is stopped so as not to move to an unexpected position.

Next, the medical personnel operates the touch panel included in the operation section 164, whereby the robot control device 150 which has received an operation command from the instruction device 200 positions the arm base 60 by moving the positioner 30 so that the arm base 60 and the operating table 300 or the patient P have a predetermined positional relationship.

Next, the medical personnel operates an arm operating device (not shown) provided in each of the robot arms 70 so that a sleeve (cannula sleeve) left on the body surface of the patient P and the medical instrument 140 have a predetermined initial positional relationship and thereby operates each of the robot arms 70 to position the medical instrument 140. The positioning operation of the positioner 30 and the positioning operation of each of the robot arms 70 may be performed simultaneously. Then, in principle, the robot control device 150 operates the medical instrument 140 by each of the robot arms 70 in response to an operation command from the instruction device 200 while the positioner 30 is stationary, and performs operation while appropriately displacing the medical instrument 140 and changing the posture.

Subsequently, a detailed configuration of the robot arm 70 will be described. As shown in FIG. 2, the robot arm 70 includes an arm body 80 and a translation unit 90 connected to a distal end of the arm body 80, and is configured to be able to move the distal end in a three-dimensional space with respect to the proximal end.

In the present embodiment, the plurality of robot arms 70 included in the medical manipulator 20 have the same or similar configurations. However, at least one of the plurality of robot arms 70 may have a configuration different from the other arms. At a distal end of the robot arm 70, a holder 96 capable of holding the medical instrument 140 is provided.

The medical instrument 140 includes a drive unit 142 provided at the proximal end, an end effector (surgical tool) 144 provided at the distal end, and an elongated shaft 146 which connects between the drive unit 142 and the end effector 144. The drive unit 142, the shaft 146, and the end effector 144 are arranged along a long axis direction Dt.

The robot arm 70 is configured to be detachable from the arm base 60. The robot arm 70 has water resistance, heat resistance, and chemical resistance for cleaning and sterilization. There are various methods for sterilizing the robot arm 70. For example, a high-pressure steam sterilization method, an EOG sterilization method, a chemical disinfecting method using a disinfectant, or the like is selectively used.

The arm body 80 includes a base 82 detachably attached to the arm base 60, and links 84a to 84f sequentially connected from the base 82 toward the distal end. More specifically, a proximal end of the link 84a is connected to the distal end of the base 82 through a torsion joint shaft J81. A proximal end of the link 84b is connected to a distal end of the link 84a through a bending joint shaft J82. A proximal end of the link 84c is connected to a distal end of the link 84a through a torsion joint shaft J83. A proximal end of the link 84d is connected to a distal end of the link 84c through a bending joint shaft J84. A proximal end of the link 84e is connected to a distal end of the link 84d through a torsion joint shaft J85. A proximal end of the link 84f is connected to a distal end of the link 84e through a bending joint shaft J86. A proximal end of the translation unit 90 is connected to a distal end of the link 86f through a bending joint shaft J87.

According to the above configuration, the robot arm 70 is configured as a multi-jointed (seven-axis articulated) arm with a degree of freedom (seven degrees of freedom). Therefore, the posture of the robot arm 70 can be changed without changing the position of the distal end of the robot arm 70.

An outer shell of the arm body 80 is mainly formed of a member having heat resistance and chemical resistance such as stainless steel. A seal (not shown) for providing water resistance is provided at a connection portion between the links. This seal has heat resistance corresponding to a high-pressure steam sterilization method and chemical resistance to disinfectants. At the connection portion between the links, an end of one link is inserted inside an end of the other link to be connected, and a seal is disposed so as to fill between the ends of these links, whereby the seal is hidden from an external appearance. This suppresses intrusion of water, chemicals, vapor, and the like from between the seal and the link.

The translation unit 90 translates a holder 96, attached to a distal end of the translation unit 90, in the long axis direction Dt and thereby translates the medical instrument 140, attached to the holder 96, in an extending direction of the shaft 146.

The translation unit 90 includes, at a distal end of the sixth link 84f of the arm body 80, a proximal end side link 91a connected through the bending joint shaft J87, a distal end side link 91b, a connecting link 92 that moves in conjunction between the proximal end side link 91a and the distal end side link 91b, and an interlocking mechanism (not shown). The bending joint shaft J87 extends in a direction orthogonal to the long axis direction Dt. A rotation shaft 64 is provided at a distal end of the translation unit 90, that is, at the distal end of the distal end side link 91b. The distal end side link 91a includes a drive source of the translation unit 90. The connecting link 92 extends along the long axis direction Dt.

In such a configuration, in the translation unit 90, the interlocking mechanism changes a relative position in the long axis direction Dt between the proximal end side link 91a and the connecting link 92 and a relative position in the long axis direction Dt between the connecting link 92 and the distal end side link 91b, whereby a position with respect to the long axis direction Dt of the medical instrument 140 held by the holder 96 provided in the distal end side link 91b with respect to the proximal end side link 91a can be changed.

Next, as shown in FIG. 3, the robot arm 70 includes, corresponding to the respective joint shafts J81 to J87, servomotors M81 to M87 (motors) for drive, encoders E81 to E87 that detect rotation angles of the servomotors M81 to M87, and a speed reducer (not shown) that decelerates output of the servomotors M81 to M87 to increase a torque. In addition, the translation unit 90 includes a servomotor M88 for a translation operation, a servomotor M89 for a rotation operation around a rotation axis 99, encoders E88 and E89 that detect rotation angles of the servomotors M88 and M89, and a speed reducer (not shown) that decelerates output of the servomotors M88 and M89 to increase a torque. FIG. 3 representatively shows the servomotors M81 and M89 among the servomotors M81 to M89, representatively shows the encoders E81 and E89 among the encoders E81 to E89, and omits a control system of the other joint shafts J82 to J87.

Then, a first non-excitation-actuated electromagnetic brake 81 (1) and a second non-excitation-actuated electromagnetic brake 81 (2) (a plurality of non-excitation-actuated electromagnetic brakes) are attached to the servomotor M81. Then, in order to control the operation of each of the first non-excitation-actuated electromagnetic brake 81 (1) and the second non-excitation-actuated electromagnetic brake 81 (2), the control device 170A for a non-excitation-actuated electromagnetic brake according to the present embodiment is provided. In the present embodiment, a multi-brake system including a plurality of non-excitation-actuated electromagnetic brakes is configured as described above.

Two non-excitation-actuated electromagnetic brakes are similarly attached to each of the servomotors M82 to M89 of the robot arm 70A. As shown in FIG. 3, operations of the first non-excitation-actuated electromagnetic brakes B81 (1) to B89 (1) and the second non-excitation-actuated electromagnetic brakes B81 (2) to B89 (2) provided respectively on the servomotors M81 to M89 of the robot arm 70A are controlled by the single control device 170A for a non-excitation-actuated electromagnetic brake.

Similarly, two non-excitation-actuated electromagnetic brakes are similarly attached to each of the servomotors M31 to M37 of the positioner 30. As shown in FIG. 3, operations of the first non-excitation-actuated electromagnetic brakes B31 (1) to B37 (1) and the second non-excitation-actuated electromagnetic brakes B31 (2) to B37 (2) provided respectively on the servomotors M31 to M37 of the positioner 30 are controlled by the single control device 170A for a non-excitation-actuated electromagnetic brake, which is separately provided from the control device 170A for a non-excitation-actuated electromagnetic brake for the robot arm 70A.

The multi-brake system may operate the first non-excitation-actuated electromagnetic brake B81 (1) and the second non-excitation-actuated electromagnetic brake B81 (2) similarly, based on the same operation command from the control device 170A for a non-excitation-actuated electromagnetic brake. Consequently, safety of the surgical operation system 10 can be improved.

As shown in FIG. 3, the positioner 30 includes, corresponding to the respective joint shafts J31 to J37 of the positioner 30, the servomotors M31 to M37 for drive, encoders E31 to E37 that detect rotation angles of the servomotors M31 to M37, and a speed reducer (not shown) that decelerates output of the servomotors M31 to M37 to increase a torque. FIG. 3 representatively shows a control system of the joint shafts J31 and J37 among the joint shafts J31 to J37 of the positioner 30 and omits a control system of the other joint shafts J32 to J36.

The robot control device 150 includes an arm control section 151 that controls movement of the plurality of robot arms 70 based on an operation command, and a positioner control section 152 that controls movement of the positioner 30. Servo control sections C81 to C89 are electrically connected to the arm control section 151. The encoders E81 to E89 are electrically connected to the servo control sections C81 to C89. Servo control sections C31 to C37 are electrically connected to the positioner control section 152. The encoders E31 to E37 are electrically connected to the servo control sections C31 to C37.

Based on an operation command input to the instruction device 200, a position/posture command of the distal end of the robot arm 70 is input to the arm control section 151. The arm control section 151 generates and outputs a position command value based on the position/posture command and the rotation angles detected by the encoders E81 to E89. The servo control sections C81 to C89 that have obtained the position command value generate and output a drive command value (torque command value) based on the rotation angle and the position command value detected by the encoders E81 to E89. An amplifier circuit that has obtained the drive command value supplies a drive current corresponding to the drive command value to the servomotors M81 to M89. In this way, the servomotors M81 to MM89 are servo-controlled so that the distal end of the robot arm 70 reaches the position and posture corresponding to the position/posture command.

The robot control device 150 includes the storage section 160 from which data can be read to the arm control section 151. Surgery information input via the instruction device 200 is stored in the storage section 160 in advance.

The positioner control section 152 generates and outputs a position command value based on an operation command related to setting of a preparation position and the like input from an operating device 162 and the rotation angles detected by the encoders E31 to E37. The servo control sections C31 to C37 that have obtained the position command value generate and output a drive command value (torque command value) based on the rotation angle and the position command value detected by the encoders E31 to E37. An amplifier circuit that has obtained the drive command value supplies a drive current corresponding to the drive command value to the servomotors M31 to M37. In this way, the servomotors M31 to M37 are servo-controlled so that the positioner 30 reaches the position/posture corresponding to the position command value.

(Servomotor M81)

FIG. 4 is a cross-sectional view along an axial direction showing an internal configuration of each of a servomotor, an encoder, and a non-excitation-actuated electromagnetic brake provided in the medical manipulator according to the present embodiment. In the following, the "load side" is a direction in which a load is attached to the servomotor M81, that is, in this example, a direction in which a shaft 102 protrudes (the lower side in FIG. 4). The "anti-load side" is a direction opposite to the load side (the upper side in FIG. 4). The same configuration as the servomotor M81, the encoder E81, and the non-excitation-actuated electromagnetic brake B81 in the joint shaft J81 shown in FIG. 4 is provided for each of the servomotors M82 to M89 and M31 to M37. However, only the structure of the servomotor M81 (i.e., the joint shaft J81) will be described here, and other similar description will not be repeated.

As shown in FIG. 4, the servomotor M81 includes a frame 101, a shaft 102, a load-side bracket 103 provided at a load-side end of the frame 101, and an anti-load-side bracket 104 (hereinafter, also referred to as a plate) provided at an anti-load-side end of the frame 101. The load-side bracket 103 and the anti-load-side bracket 104 (plate) are provided with a load-side bearing and an anti-load-side bearing (not shown), respectively, and the shaft 102 is rotatably supported via these bearings.

The servomotor M81 has a rotor 105 provided on the shaft 102 and a stator 106 provided on an inner peripheral surface of the frame 101. The rotor 105 is provided with, for example, a plurality of permanent magnets (not shown). The stator 106 has a stator core (not shown) disposed in an annular shape and a plurality of armature windings (not shown) wound around a plurality of teeth of the stator core.

(Non-Excitation-Actuated Electromagnetic Brake B81)

As shown in FIG. 4, the servomotor M81 is provided with the non-excitation-actuated electromagnetic brake B81. Although a case where the single non-excitation-actuated electromagnetic brake B81 is provided for the servomotor M81 is shown here to avoid complexity of appearance, in the present embodiment, as described with reference to FIG. 3, the servomotor M81 is provided with two non-excitation-actuated electromagnetic brakes B81 (the first non-excitation-actuated electromagnetic brake B81 (1) and the second non-excitation-actuated electromagnetic brake B81 (2)).

The non-excitation-actuated electromagnetic brake B81 is disposed on the anti-load side of the servomotor M81, and the shaft 102 is stopped and held or braked. The non-excitation-actuated electromagnetic brake B81 is configured to apply the brake when a coil 113 described later is in the non-excited state, and not to apply the brake when the coil 113 is in the excited state.

The non-excitation-actuated electromagnetic brake B81 may be disposed on the load side of the servomotor M81. The non-excitation-actuated electromagnetic brake B81 is covered by a brake cover (not shown). The non-excitation-actuated electromagnetic brake B81 has a cylindrical field core 117, an annular armature 118 disposed facing the load side of the field core 117, and a brake disc 119 disposed between the armature 118 and a plate 104 (anti-load-side bracket).

The field core 117 is fixed to the plate 104 by a bolt 111. The field core 117 is provided with a plurality of braking springs 112. The braking spring 112 presses the armature 118 to urge the armature 118 toward the load. The field core 117 is provided with the coil 113. The coil 113 generates a magnetic attraction force when energized, and attracts the armature 118 to the anti-load side against the biasing force of the braking spring 112. The armature 118 is made of a magnetic material (such as a steel plate).

The brake disc 119 is fixed to the shaft 102 via a hub 114. An annular friction plate 115 is attached to both the load side and the anti-load side of the brake disc 119. The brake disc 119 is configured to be slidable in an axial direction of the shaft 102.

In the non-excitation-actuated electromagnetic brake B81, when the coil 113 is in the non-excited state, the armature 118 is pressed toward the plate 104 (load side) by the biasing force of the braking spring 112. The brake disc 119 and the friction plate 115 are sandwiched between the armature 118 and the plate 104. At this time, a gap G occurs between the field core 117 and the armature 118. As a result, the stopping and holding or the rotation of the shaft 102 is braked when a power supply is cut off. This state is a state where the non-excitation-actuated electromagnetic brake B81 is applied.

On the other hand, when the coil 113 is in the excited state, the armature 118 moves toward the coil 113 (anti-load side) due to the magnetic attraction force of the coil 113. A space corresponding to the gap G is generated between the armature 118 and the plate 104, and the brake disc 119 and the friction plate 115 become free. As a result, the brake disc 119 is released from the braking operation when the servomotor M81 is operating, and the shaft 102 can rotate. This state is a state where the non-excitation-actuated electromagnetic brake B81 is released.

The encoder E81 is disposed on the anti-load side of the non-excitation-actuated electromagnetic brake B81 and is connected to the shaft 102. The encoder E81 may be disposed in another manner (for example, disposed between the servomotor M81 and the non-excitation-actuated electromagnetic brake B81). Then, the encoder E81 detects the rotational position (the rotation angle or the like) of the shaft 102 to detect the rotation position of the servomotor M81, and thus to output data of the detected position. In addition to or instead of the rotational position of the servomotor M81, the encoder E81 may detect at least one of a speed (for example, a rotational speed and an angular speed) of the servomotor M81 and an acceleration (for example, a rotational acceleration and an angular acceleration) of the servomotor M81.

(Control Device 170A for a Non-Excitation-Actuated Electromagnetic Brake)

FIG. 5 is a circuit diagram showing a configuration of a main portion of the control device for a non-excitation-actuated electromagnetic brake according to the present embodiment. As shown in FIG. 5, the control device 170A for a non-excitation-actuated electromagnetic brake (hereinafter may be simply referred to as "control device 170A") according to the present embodiment includes a diode 198 connected in parallel with the coil 113 provided in the non-excitation-actuated electromagnetic brake B81 so that a cathode is located on a side having a higher potential than an anode.

The control device 170A includes a Zener diode 180A (electronic component) which includes two electrodes 181a and 181b and has a characteristic that when the inter-terminal voltage of the two electrodes 181a and 181b is equal to or higher than a predetermined voltage, the resistance value is lower than when the voltage is lower than the predetermined voltage. The predetermined voltage used herein is a breakdown voltage of the Zener diode 180A. The breakdown voltage may be set to, for example, about 33 V. When such a breakdown voltage is set, an excitation voltage applied to the coil 113 provided in the non-excitation-actuated electromagnetic brake B81 in order to bring the coil 113 into the excited state may be set to about 24 V.

The coil 113 provided in the non-excitation-actuated electromagnetic brake B81 and the Zener diode 180A are connected in series to form a first series circuit, and the first series circuit and the diode 198 are connected in parallel to form a first parallel circuit. In the present embodiment, an npn transistor 192 is provided on a side having a higher potential than the first parallel circuit, and an npn transistor 194 is provided on a side having a lower potential than the first parallel circuit. When both of the npn transistors 192 and 194 are turned on, the coil 113 enters an excited state. When at least one of the npn transistors 192 and 194 is turned off, the coil 113 enters the non-excited state. With such a configuration, the safety of the surgical operation system 10 can be improved.

The Zener diode 180A is connected in series with the coil 113 so as not to be conducted when the inter-terminal voltage is lower than the predetermined voltage, but to be conducted when the inter-terminal voltage becomes equal to or higher than the predetermined voltage. Specifically, the Zener diode 180A is connected in series with the coil 113 so that a cathode of the Zener diode 180A is located on the coil 113 side and an anode of the Zener diode 180A is located on the ground side. The conduction here is not limited to a case where the Zener diode 180A is conducted because the resistance value of the Zener diode 180A is 0Ω (or almost 0Ω), but also includes a case where the Zener diode 180A is conducted because an impedance (resistance value) of the Zener diode 180A is sufficiently smaller than an impedance of the coil 113.

The control device 170A according to the present embodiment is connected in parallel with the Zener diode 180A (electronic component) so as to be a bypass for the Zener diode 180A, and further includes an npn transistor 190A (switching element) capable of switching a state between a state where the Zener diode 180A functions effectively and a state where the Zener diode 180A does not function. In the npn transistor 190A, a collector is connected to the electrode 181a of the Zener diode 180A, and an emitter is connected to the electrode 181b of the Zener diode 180A, so that the npn transistor 190A is connected in parallel with the Zener diode 180A.

As shown in the block diagram of FIG. 3, the control device 170A according to the present embodiment includes a storage section 172 and a processor 174 for executing a program stored in the storage section 172. The control device 170A may be configured as a part of the robot control device 150. Moreover, the storage section 172 of the control device 170A may be configured as a part of the storage section 160 of the robot control device 150.

The control device 170A according to the present embodiment may be provided for each of the robot arms 70A to 70D and the positioner 30. In FIG. 3, the control device 170A provided in the robot arm 70A is described separately from the arm control section 151, but may be configured as a part of the arm control section 151. Similarly, 170A provided in the positioner 30 may be configured as a part of the positioner control section 152.

Next, an example of processing executed by the control device 170A will be described with reference to FIG. 6. FIG. 6 is a flowchart showing the example of the processing executed by the control device for a non-excitation-actuated electromagnetic brake according to the present embodiment.

First, the control device 170A turns off the npn transistor 190A so that the Zener diode 180A functions effectively (step S1 in FIG. 6).

Next, when the rotation of the servomotor M81 is about to be stopped by a servo ring ("YES" in step S2 of FIG. 6), the npn transistor 190A is turned on so that the Zener diode 180A does not function effectively (step S3 in FIG. 6).

The control device 170A returns to step S2 and repeats the processing when the rotation of the servomotor M81 is not about to be stopped by the servo ring ("NO" in step S2 in FIG. 6).

(Effect)

The control device 170A for the non-excitation-actuated electromagnetic brake according to the present embodiment can prevent a surge current from flowing through the coil 113 provided in the non-excitation-actuated electromagnetic brake B81 by connecting the diode 198 in parallel with the coil 113. The control device 170A includes the Zener diode 180A (electronic component) connected in series with the coil 113 provided in the non-excitation-actuated electromagnetic brake B81 so that the Zener diode 180A is not conducted when the inter-terminal voltage (ie, a potential difference between the electrodes 181a and 181b) is lower than a predetermined voltage, but conducted when the inter-terminal voltage (the potential difference between the electrodes 181a and 181b) becomes equal to or higher than the predetermined voltage, so that it is possible to prevent a return current from flowing through the coil 113. Consequently, it is possible to prevent a delay from occurring until the brake is applied.

The control device 170A according to the present embodiment further includes the npn transistor 190A (switching element) connected in parallel with the Zener diode 180A (electronic component) so as to be a bypass for the Zener diode 180A, so that it is possible to switch the state between the state where the Zener diode 180A functions effectively and the state where the Zener diode 180A does not function according to the situation.

Moreover, in the present embodiment, the breakdown voltage (predetermined voltage) of the Zener diode 180A is set to 120% or more and 200% or less of the excitation voltage, so that it is possible to further suppress the occurrence of a delay until the brake is applied, as compared with a case where the breakdown voltage is less than 120% of the excitation voltage. Noise can be suppressed as compared with a case where the breakdown voltage is higher than 200% of the excitation voltage.

In the present embodiment, when the rotation of the servomotor M81 is about to be stopped by the servo ring, the npn transistor 190A is turned on so that the Zener diode 180A does not function effectively, so that it is possible to prevent wear from occurring between the servomotor M81 and the non-excitation-actuated electromagnetic brake B81 (more specifically, the first non-excitation-actuated electromagnetic brake 81 (1) and the second non-excitation-actuated electromagnetic brake 81 (1)), and to suppress noise that may occur when the non-excitation-actuated electromagnetic brake B81 is applied quickly.

When the Zener diode 180A (electronic component) functions effectively, for example, if a failure occurs in a system, or if a surge current flows due to a lightning strike, an error signal indicating the fact is detected by the servo control section C81, and the signal reception turns off at least one of the npn transistors 192 and 194, so that the coil 113 may be brought into the non-excited state, and the brake may be applied quickly. Alternatively, the coil 113 is brought into the non-excited state during operation to apply the brake quickly, so that safety can be improved. Improving the safety in this way is particularly effective in the surgical operation system 10 (medical robotic system).

When the rotation of the servomotor M81 is about to be stopped by the servo ring, the npn transistor 190A is turned on so that the Zener diode 180A does not function effectively, so that it is possible to prevent wear from occurring between the servomotor and the non-excitation-actuated electromagnetic brake, and to suppress noise that may occur when the non-excitation-actuated electromagnetic brake B81 is applied quickly.

(Modification)

Numerous modifications and alternative embodiments of the invention will be apparent to those skilled in the art in view of the foregoing description. Therefore, the foregoing explanation should be interpreted only as an example and is provided for the purpose of teaching the best mode for carrying out the present invention to one skilled in the art. The structures and/or functional details may be substantially modified within the spirit of the present invention.

(First Modification)

With reference to FIG. 7, a first modification of the control device for a non-excitation-actuated electromagnetic brake according to the above embodiment will be described. FIG. 7 is a circuit diagram showing a configuration of a main portion of a first modification of the control device for a non-excitation-actuated electromagnetic brake according to the above embodiment. The control device 170B according to the present modification has the same configuration as the control device 170A according to the above embodiment, except that the control device 170B includes a field effect transistor 190B instead of the npn transistor 190A. Therefore, the same portions are denoted by the same reference numerals, and the repeated description thereof will be omitted.

As shown in FIG. 7, the control device 170B for a non-excitation-actuated electromagnetic brake according to the present modification is connected in parallel with the Zener diode 180A (electronic component) so as to be a bypass for the Zener diode 180A, and includes the field effect transistor 190B (switching element) capable of switching the state between the state where the Zener diode 180A functions effectively and the state where the Zener diode 180A does not function. The control device for a non-excitation-actuated electromagnetic brake may have such a configuration.

(Second Modification)

With reference to FIG. 8, a second modification of the control device for a non-excitation-actuated electromagnetic brake according to the above embodiment will be described. FIG. 8 is a circuit diagram showing a configuration of a main portion of a second modification of the control device for a non-excitation-actuated electromagnetic brake according to the above embodiment. The control device 170C according to the present modification has the same configuration as the control device 170A according to the above embodiment, except that the control device 170C includes a varistor 180B instead of the Zener diode 180A. Therefore, the same portions are denoted by the same reference numerals, and the repeated description thereof will be omitted.

As shown in FIG. 8, the control device 170C for a non-excitation-actuated electromagnetic brake according to the present modification includes a varistor 180B (electronic component) which includes the two electrodes 181a and 181b and in which when the inter-terminal voltage of the two electrodes 181a and 181b is equal to or higher than a predetermined voltage, the resistance value is lower than when the voltage is lower than the predetermined voltage. The predetermined voltage used here is a varistor voltage of the varistor 180B. The control device for a non-excitation-actuated electromagnetic brake may have such a configuration.

(Third Modification)

With reference to FIG. 9, a third modification of the control device for a non-excitation-actuated electromagnetic brake according to the above embodiment will be described. FIG. 9 is a circuit diagram showing a configuration of a main portion of a third modification of the control device for a non-excitation-actuated electromagnetic brake according to the above embodiment. The control device 170D according to the present modification has the same configuration as the control device 170A according to the above embodiment, except that the npn transistor 190A is not provided. Therefore, the same portions are denoted by the same reference numerals, and the repeated description thereof will be omitted.

As shown in FIG. 9, the control device 170D for a non-excitation-actuated electromagnetic brake according to the present modification does not include the npn transistor 190A (switching element), unlike the control device 170A according to the above embodiment. Thus, the control device 170D has a simpler configuration.

(Other Modifications)

In the above embodiment and the first to third modifications, the case where the electronic component connected in series with the coil 113 so as not to be conducted when the inter-terminal voltage of the two electrodes 181a and 181b is lower than a predetermined voltage, but to be conducted when the inter-terminal voltage becomes equal to or higher than the predetermined voltage is the Zener diode 180A or the varistor 180B has been described, but the present invention is not limited to this case. For example, the electronic component may be a chip-type multilayer ceramic capacitor, or may be an electrostatic discharge suppressor. Alternatively, any electronic component may be used as long as it can be connected in series with the coil 113 so as not to be conducted when the inter-terminal voltage of the two electrodes 181a and 181b is lower than a predetermined voltage, but to be conducted when the inter-terminal voltage becomes equal to or higher than the predetermined voltage.

In the above embodiment, the case where the breakdown voltage of the Zener diode 180A is set to about 33 V, and the excitation voltage applied to the coil 113 provided in the non-excitation-actuated electromagnetic brake B81 is set to about 24 V in order to bring the coil 113 into the excited state has been described, but the present invention is not limited to this case. For example, the breakdown voltage of the Zener diode 180A may be set to 120% or more and 200% or less of the excitation voltage. When an electronic component having a characteristic that when the inter-terminal voltage is equal to or higher than a predetermined voltage, the resistance value is lower than when the voltage is lower than the predetermined voltage is provided in place of the Zener diode 180A, the predetermined voltage may be set to, for example, 120% or more and 200% or less of the excitation voltage.

In the above embodiment and the first to third modifications, the case where the Zener diode 180A or the varistor 180B is connected in series with the coil 113, provided in the non-excitation-actuated electromagnetic brake B81, on the side having a lower potential than the coil 113 has been described, but the present invention is not limited to this case.

For example, the Zener diode 180A or the varistor 180B may be connected in series with the coil 113 on a side having a higher potential than the coil 113 by appropriately changing the circuit configuration, or may be connected in series with the coil 113 on both the side having a lower potential and the side a higher potential than the coil 113 provided in the non-excitation-actuated electromagnetic brake B81.

A plurality of the Zener diodes 180A or a plurality of the varistors 180B may be connected in series with the coil 113, provided in the non-excitation-actuated electromagnetic brake B81, on the side having a lower potential than the coil 113 or may be connected in series with the coil 113 on the side having a higher potential than the coil 113.

The same is true for a case where, in place of the Zener diode 180A or the varistor 180B, an electronic component having a characteristic that when the inter-terminal voltage is equal to or higher than a predetermined voltage, the resistance value is lower than when the voltage is lower than the predetermined voltage is connected in series with the coil 113. Different types of electronic components having the above characteristic may be connected in series with the coil 113.

In the above embodiment, the case where when the rotation of the servomotor M81 is about to be stopped by the servo ring, the npn transistor 190A is turned on so that the Zener diode 180A does not function effectively has been described. However, the present invention is not limited to this case, and when the rotation of the servomotor M81 is about to be stopped by the servo ring, the npn transistor 190A may be turned off so that the Zener diode 180A functions effectively. Although this may cause wear between the servomotor M81 and the non-excitation-actuated electromagnetic brake B81, it is possible to improve safety by quickly applying the brake. Improving the safety in this way is particularly effective in the surgical operation system 10 (medical robotic system).

In the above embodiment and the first to third modifications, the case where the switching element capable of switching the state between the state where the Zener diode 180A or the varistor 180B (electronic component) functions effectively and the state where the electronic component does not function is the npn transistor 190A or the field effect transistor 190B has been described, but the present invention is not limited to this case. For example, the npn transistor 190A may be replaced with a pnp transistor by inverting an input signal to the base. Alternatively, the switching element may be a relay circuit, an insulated gate bipolar transistor (so-called "IGBT"), or another switching element as long as it can switch the state between the state where the electronic component functions effectively and the state where the electronic component does not function.

In the above embodiment, there has been described the case where the first series circuit (a series circuit formed by connecting the coil 113 and the Zener diode 180A in series) and the diode 198 are connected in parallel to form the first parallel circuit, the npn transistor 192 is provided on the side having a higher potential than the first parallel circuit, and the npn transistor 194 is provided on the side having a lower potential than the first parallel circuit. However, the present invention is not limited to this case, and the npn transistors 192 and 194 may be replaced with field effect transistors, relay circuits, or insulated gate bipolar transistors (so-called "IGBTs"), or other switching elements. The npn transistors 192 and 194 may be replaced with switching elements different from each other.

In the above embodiment and the first to third modifications, the case where the control device 170 for a non-excitation-actuated electromagnetic brake is applied to the plurality of robot arms 70 and the positioner 30 of the surgical operation system 10 has been described, but the present invention is not limited to this case. For example, the control device 170 for a non-excitation-actuated electromagnetic brake may be applied to the operation arm 202 for the practitioner S in the surgical operation system 10 to input an operation command.

Alternatively, the control device 170 for a non-excitation-actuated electromagnetic brake may be used in another robot system using the non-excitation-actuated electromagnetic brake. A structure of a robot to which the non-excitation-actuated electromagnetic brake is applied is not limited to the structure shown in FIGS. 1 to 3, and the robot may be, for example, a vertical articulated-type robot having 1 or more and 5 or less axes or 8 or more axes. Alternatively, the robot to which the non-excitation-actuated electromagnetic brake is applied may be a polar coordinate type robot, a cylindrical coordinate type robot, a rectangular coordinate type robot, or a robot having another structure.

(Experimental Example)

Lastly, an experimental example performed by the inventors to confirm the effect of the present invention will be described with reference to FIGS. 10A and 10B. FIG. 10A is a graph showing results of an experiment performed by the present inventors to confirm an effect of the control device for a non-excitation-actuated electromagnetic brake according to the above embodiment, and a graph when the coil is switched to a non-excited state after the Zener diode is enabled. FIG. 10B is a graph showing results of an experiment performed by the present inventors to confirm an effect of the control device for a non-excitation-actuated electromagnetic brake according to the above embodiment, and a graph when the coil is switched to a non-excited state after the Zener diode is disabled.

An experiment was performed using a circuit configuration, shown in FIG. 5, provided in the control device 170A according to the above embodiment. The breakdown voltage of the Zener diode 180A was set to 33 V. The excitation voltage applied to the coil 113 provided in the non-excitation-actuated electromagnetic brake B81 was set to 24 V in order to bring the coil 113 into the excited state.

Data on the upper side of FIG. 10A is a current value flowing through the coil 113 when the coil 113 is switched to the non-excited state after the Zener diode 180A is enabled by the control device 170A according to the above embodiment. Data on the lower side of FIG. 10A is the inter-terminal voltage of the coil 113 at the same time.

On the other hand, data on the upper side of FIG. 10B is a current value flowing through the coil 113 when the coil 113 is switched to the non-excited state after the Zener diode 180A is disabled by the control device 170A according to the above embodiment. Data on the lower side of FIG. 10B is the inter-terminal voltage of the coil 113 at the same time.

As shown in FIG. 10A, when the coil 113 is switched to the non-excited state after the Zener diode 180A is enabled, the current flowing through the coil 113 disappears quickly. That is, no return current flows through the coil 113. Consequently, it is possible to prevent a delay from occurring until the brake is applied.

On the other hand, as shown in FIG. 10B, when the coil 113 is switched to the non-excited state after the Zener diode 180A is disabled, the current flowing through the coil 113 does not disappear quickly but gradually decreases over a certain period of time. That is, at this time, a return current flows through the coil 113, and a delay occurs until the brake is applied. However, on the other hand, at this time, as can be understood from the data on the lower side of FIG. 10B, compared to a case shown in FIG. 10A, noise that may occur when the non-excitation-actuated electromagnetic brake B81 is applied quickly can be suppressed. As compared with a case shown in FIG. 10A, it is possible to prevent wear from occurring between the servomotor M81 and the non-excitation-actuated electromagnetic brake B81.

As described above, it is preferable that the state where the Zener diode 180A functions effectively and the state where the Zener diode 180A does not function be switched by the npn transistor 190A (switching element) according to the situation (for example, as described with reference to the flowchart of FIG. 6).

The invention claimed is:

1. A control device for controlling operation of a non-excitation-actuated electromagnetic brake, which applies the brake when a coil of the brake is in a non-excited state and does not apply the brake when the coil is in an excited state, the control device comprising:
   an electronic component comprising two electrodes and having a characteristic that when an inter-terminal voltage of the two electrodes is equal to or higher than a predetermined voltage, a resistance value of the electronic component is lower than when the voltage is lower than the predetermined voltage; and
   a diode disposed such that a cathode is located on a side having a higher potential than an anode, wherein
   the coil is provided in the non-excitation-actuated electromagnetic brake, and the coil and the electronic component are connected in series to form a first series circuit, the first series circuit and the diode are connected in parallel,
   the electronic component is connected in series with the coil provided in the non-excitation-actuated electromagnetic brake so as not to be conducted when the inter-terminal voltage is lower than the predetermined voltage, and so as to be conducted when the inter-terminal voltage becomes equal to or higher than the predetermined voltage, and
   the predetermined voltage is set to 120% or more and 200% or less of an excitation voltage applied to the coil, provided in the non-excitation-actuated electromagnetic brake, in order to bring the coil into an excited state.

2. The control device for a non-excitation-actuated electromagnetic brake according to claim 1, wherein the electronic component is a Zener diode or a varistor.

3. The control device for a non-excitation-actuated electromagnetic brake according to claim 1, further comprising a switching element which is connected in parallel with the electronic component such that the switching element is a bypass for the electronic component and switches between a state where the electronic component is enabled and a state where the electronic component is disabled.

4. The control device for a non-excitation-actuated electromagnetic brake according to claim 3, wherein the switching element is a transistor or a field effect transistor.

5. The control device for a non-excitation-actuated electromagnetic brake according to claim 3, wherein the non-excitation-actuated electromagnetic brake is attached to a motor to apply a brake to the motor.

6. A robot comprising:
   the control device for a non-excitation-actuated electromagnetic brake according to claim 5,
   the non-excitation-actuated electromagnetic brake;
   the motor to which the non-excitation-actuated electromagnetic brake is attached;
   a robot arm having at least one joint shaft driven by the motor; and
   a robot control device for controlling operation of the motor.

7. The robot according to claim 6, further comprising:
   a multi-brake system comprising a plurality of non-excitation-actuated electromagnetic brakes and the control device for controlling operation of each of the plurality of non-excitation-actuated electromagnetic brakes,
   wherein the control device is configured to control operation of a non-excitation-actuated electromagnetic brake which applies the brake when a coil of the brake is in a non-excited state and does not apply the brake when the coil is in an excited state.

8. The robot according to claim 6, wherein the control device for a non-excitation-actuated electromagnetic brake is a part of the robot control device.

9. A medical robotic system comprising the robot according to claim 6.

10. A medical robotic system comprising:
a robot arm comprising a non-excitation-actuated electromagnetic brake, which applies the brake when a coil of the brake is in a non-excited state and does not apply the brake when the coil is in an excited state, a motor to which the non-excitation-actuated electromagnetic brake is attached, and a joint shaft driven by the motor,
a robot control device comprising a processor configured to control operation of the motor, and
a control device configured to control operation of the non-excitation-actuated electromagnetic brake of the robot arm,
the control device comprising:
an electronic component comprising two electrodes and having a characteristic that when an inter-terminal voltage of the two electrodes is equal to or higher than a predetermined voltage, a resistance value of the electronic component is lower than when the voltage is lower than the predetermined voltage; and
a diode disposed such that a cathode is located on a side having a higher potential than an anode, wherein
the coil and the electronic component are connected in series to form a first series circuit, the first series circuit and the diode are connected in parallel,
the electronic component is connected in series with the coil provided in the non-excitation-actuated electromagnetic brake such that the electronic component is not conducted when the inter-terminal voltage is lower than the predetermined voltage, and is conducted when the inter-terminal voltage becomes equal to or higher than the predetermined voltage, and
the predetermined voltage is set to 120% or more and 200% or less of an excitation voltage applied to the coil, provided in the non-excitation-actuated electromagnetic brake, in order to bring the coil into an excited state.

11. The medical robotic system according to claim 10, further comprising an instruction device that allows an operator to remotely operate the robot arm,
wherein the robot arm holds a medical instrument at a distal end, and
the robot control device controls operation of the motor to operate the robot arm based on operation of the instruction device.

12. The medical robotic system according to claim 10, wherein the electronic component is a Zener diode or a varistor.

13. The medical robotic system according to claim 10, further comprising a switching element which is connected in parallel with the electronic component such that the switching element is a bypass for the electronic component and switches between a state where the electronic component functions is enabled and a state where the electronic component is disabled.

14. The medical robotic system according to claim 13, wherein the switching element is a transistor or a field effect transistor.

15. The medical robotic system according to claim 10, wherein the robot arm comprises a plurality of the joint shafts, a plurality of the motors, and a plurality of the non-excitation-actuated electromagnetic brakes, and
the system further comprises a plurality of the control devices, each control device being configured to control a non-excitation-actuated electromagnetic brake.

16. A robotic system comprising:
a robot arm comprising a motor, a first non-excitation-actuated electromagnetic brake, and a second non-excitation-actuated electromagnetic brake,
wherein the first non-excitation-actuated electromagnetic brake and the second non-excitation-actuated electromagnetic brake are attached to the motor;
a robot control device which controls operation of the motor; and
a control device which controls the first non-excitation-actuated brake,
wherein the control device comprises:
an electronic component comprising two electrodes and having a characteristic that when an inter-terminal voltage of the two electrodes is equal to or higher than a predetermined voltage, a resistance value of the electronic component is lower than when the voltage is lower than the predetermined voltage; and
a diode disposed such that a cathode is located on a side having a higher potential than an anode,
wherein a coil is provided in the first non-excitation-actuated electromagnetic brake, and the coil and the electronic component are connected in series to form a first series circuit, the first series circuit and the diode are connected in parallel, and the electronic component is connected in series with the coil provided in the non-excitation-actuated electromagnetic brake so as not to be conducted when the inter-terminal voltage is lower than the predetermined voltage, and so as to be conducted when the inter-terminal voltage is equal to or higher than the predetermined voltage,
wherein the first non-excitation-actuated electromagnetic brake and the second non-excitation-actuated electromagnetic brake are controlled by the control device, and
wherein the predetermined voltage is set to 120% or more and 200% or less of an excitation voltage applied to the coil, provided in the non-excitation-actuated electromagnetic brake, in order to bring the coil into an excited state.

17. A control device for controlling operation of a non-excitation-actuated electromagnetic brake attached to a motor, which brakes the motor when a coil of the brake is in a non-excited state and does not brake the motor when the coil is in an excited state, the control device comprising:
an electronic component comprising two electrodes and having a characteristic that when an inter-terminal voltage of the two electrodes is equal to or higher than a predetermined voltage, a resistance value of the electronic component is lower than when the voltage is lower than the predetermined voltage;
a diode disposed such that a cathode is located on a side having a higher potential than an anode, wherein the coil is provided in the non-excitation-actuated electromagnetic brake, and the coil and the electronic component are connected in series to form a first series circuit, the first series circuit and the diode are connected in parallel to form a first parallel circuit, and the electronic component is not conducted when the inter-terminal voltage is lower than the predetermined voltage, and is conducted when the inter-terminal voltage becomes equal to or higher than the predetermined voltage;

a first switching element which is connected in series with the first parallel circuit and switches a state of coil between the non-excited state and the excited state;

a second switching element which is connected in parallel with the electronic component such that the second switching element is a bypass for the electronic component and switches between a state where the electronic component is enabled and a state where the electronic component is disabled, the electronic component controls a return current through the coil in the state where the electronic component is enabled by the second switching element, a storage section; and a processor for executing a program stored in the storage section, wherein the program stored in the storage section is executed by the processor, and the first switching element switches the state of coil to the non-excited state when the electronic component is disabled by the second switching element, and wherein the predetermined voltage is set to 120% or more and 200% or less of an excitation voltage applied to the coil, provided in the non-excitation-actuated electromagnetic brake, in order to bring the coil into an excited state.

18. The control device for a non-excitation-actuated electromagnetic brake according to claim 17, comprising:

a third switching element which is connected in series with the first parallel circuit and switches a state of coil between the non-excited state and the excited state, wherein the first switching element is connected to a first side of the first parallel circuit and the third switching element is connected to a second side of the first parallel circuit, the first side having a higher potential than the first parallel circuit and the second side having a lower potential than the first parallel circuit.

* * * * *